United States Patent [19]

Hansenne

[11] Patent Number: 5,747,009
[45] Date of Patent: May 5, 1998

[54] DIHYDROXYACETONE-BASED EMULSION AND ITS USE IN COSMETICS

[75] Inventor: Isabelle Hansenne, Paris, France

[73] Assignee: L'Oreal, Paris, France

[21] Appl. No.: 530,168

[22] PCT Filed: Mar. 28, 1994

[86] PCT No.: PCT/FR94/00341

§ 371 Date: Mar. 14, 1996

§ 102(e) Date: Mar. 14, 1996

[87] PCT Pub. No.: WO94/22418

PCT Pub. Date: Oct. 13, 1994

[30] Foreign Application Priority Data

Mar. 29, 1993 [FR] France ................... 93/03600

[51] Int. Cl.⁶ .............................................. A61K 7/42
[52] U.S. Cl. .................. 424/59; 514/675; 514/937; 514/938; 514/939
[58] Field of Search ............... 424/59; 514/675, 514/937, 938, 939

[56] References Cited

U.S. PATENT DOCUMENTS 5,169,624  12/1992  Ziegler et al. ................. 424/59
5,229,104  7/1993  Sottery et al. ................. 424/59
5,547,658  8/1996  Hansenne et al. ............. 424/59

*Primary Examiner*—James J. Seidleck
*Assistant Examiner*—Michael A. Williamson
*Attorney, Agent, or Firm*—Cushman Darby & Cushman IP Group of Pillsbury Madison & Sutro LLP

[57] ABSTRACT

Stable skin coloring cosmetic emulsion comprising A) from 50 to 92% by weight, based on the total emulsion weight, of an aqueous phase containing from 0.5 to 10% by weight, based on the total emulsion weight, of dihydroxyacetone and B) from 8 to 50% by weight, based on the total emulsion weight, of a fatty phase comprising from 5 to 15% by weight of isoparaffin or poly-α-olefin, from 3 to 7% by weight of an emulsifying agent consisting of a mixture of saturated or unsaturated sorbitol and glycerol esters of $C_{18}$ fatty acids with a straight or branched chain, optionally including hydroxyl, said esters being oxyethylenated and oxypropylenated, the total number of ethylene oxide and propylene oxide being less than or equal to 5, and from 0 to 15% by weight of the additional fatty bodies, all of the percentages being based on the total emulsion weight. The water-in-oil emulsion can be used to obtain a triple water-in-oil-in-water emulsion.

13 Claims, No Drawings

DIHYDROXYACETONE-BASED EMULSION AND ITS USE IN COSMETICS

This application claims benefit of international application PCT/FR94/00341, filed Mar. 28, 1994.

The invention relates to an emulsion based on dihydroxyacetone or DHA and to the process for coloring the skin using such an emulsion.

Dihydroxyacetone or DHA is commonly used as an agent for artificially tanning the skin. In order to be applied uniformly to the skin, DHA is preferably formulated in the form of an emulsion, such as a cream or milk.

However, formulations in the emulsion form present problems of preservation on storage, in particular of stability and of development of color with time. Thus, it was possible to observe an instability of the emulsion with time, in particular when it is brought to 45° C., and a development in the coloring towards the yellows and the ambers, in particular after storing for six weeks at 45° C.

In addition, as such an emulsion is applied to the skin, research is directed at reducing the concentration of emulsifiers, which can be irritating, by as much as possible. Such an emulsion must additionally have good cosmetic properties, that is to say be easy to spread and nonsticky after application, and have good resistance to water.

The DHA-based emulsions proposed until now generally present problems of preservation after a few days or a few weeks at 45° C., take on an undesirable yellow or amber coloring or alternatively have the disadvantage of being sticky after application.

The Applicant company has discovered that by using a very specific emulsifier, in specific proportions, in a water-in-oil emulsion containing the DHA in the aqueous phase, the emulsifier being introduced into the fatty phase of the emulsion comprising specific proportions of isoparaffin or poly-α-olefin and optionally of silicone and of additional fatty substances, a composition for coloring the skin was obtained in the form of a water-in-oil emulsion which is stable on storage, which exhibits weak yellowing with time, which is nonirritating, which has good resistance to water and which has good cosmetic properties insofar as it is easy to spread and is nonsticky after application. In addition, this emulsion gives the skin an aesthetically improved coloring.

The subject of the invention is therefore a stable cosmetic emulsion for coloring the skin, of the water-in-oil type, consisting of:

A) 50 to 92% by weight, on the basis of the total weight of emulsion, of an aqueous phase comprising 0.5 to 10% by weight of dihydroxyacetone, and B) 8 to 50% by weight, on the basis of the total weight of the emulsion, of a fatty phase comprising 5 to 15% by weight of isoparaffin or of poly-α-olefin and 3 to 7% by weight of an emulsifier consisting of a mixture of sorbitol and of glycerol esters of saturated or unsaturated, straight- or branched-chain $C_{18}$ fatty acids, optionally containing a hydroxyl radical, these esters being oxyethylenated and oxypropylenated, the total number of ethylene oxide and of propylene oxide units being less than or equal to 5, all the percentages being given on the basis of the total weight of the emulsion.

The emulsion according to the invention may also contain, in the fatty phase, up to 10% by weight of silicone and/or up to 15% by weight, on the basis of the total weight of the emulsion, of additional fatty substances such as $C_8$–$C_{22}$ fatty acids, fatty alcohols, for example lauryl, cetyl, myristyl, stearyl, palmityl and oleyl alcohols, as well as 2-octyldodecanol, fatty acid esters, such as glyceryl monostearate and polyethylene glycol monostearate, and the triglycerides of $C_6$–$C_{18}$ fatty acids, such as the triglycerides of caprylic/capric acid (Miglyol 812).

Dihydroxyacetone or DHA is present in the water-in-oil emulsion according to the invention in proportions which are sufficient to confer on the skin, after application, a coloring similar to the coloring obtained following natural tanning. It is generally present in proportions of between 0.5 and 10% by weight with respect to the total weight of the emulsion and preferably between 1 and 7% by weight.

A preferred emulsifier according to the invention is the polyoxyethylenated (2.5 mol of ethylene oxide) and polyoxypropylenated (1.5 mol of propylene oxide) derivative of a mixture of the glycerol and of the sorbitol esters of hydroxystearic and isostearic acids, sold under the name "Arlacel 780" by the Company ICI.

The cosmetic water-in-oil emulsion according to the invention can be used to prepare a triple W/O/W, that is to say water-in-oil-in-water, emulsion. In such a triple emulsion, the percentage of primary W/O emulsion varies from 55 to 80% by weight with respect to the total weight of the triple emulsion. The stability of this triple emulsion is provided for by adding an emulsifier of the poly(ethylene oxide)/poly(propylene oxide) block copolymer type in proportions of 0.75 to 2% by weight with respect to the total weight of the triple emulsion.

This block copolymer is dissolved in the continuous external aqueous phase of the triple emulsion. If necessary, the external aqueous phase can contain a thickener, such as a cellulose derivative.

Another subject of the invention is therefore the use of the above W/O emulsion in the preparation of a triple W/O/W emulsion.

Another subject of the invention consists of a stable cosmetic emulsion for coloring the skin, of the triple W/O/W emulsion type, containing 55 to 80% by weight of the above W/O emulsion in 45 to 20% by weight, on the basis of the total weight of the triple emulsion, of a continuous external aqueous phase containing 0.75 to 2% by weight, with respect to the total weight of the triple emulsion, of an emulsifier of the poly(ethylene oxide)/poly(propylene oxide) block copolymer type and optionally a thickener.

A further subject of the invention is the process for coloring the skin using a W/O cosmetic emulsion as defined above or the triple W/O/W cosmetic emulsion obtained from the latter.

The isoparaffin or the poly-α-olefin used in the fatty phase of the cosmetic emulsion according to the invention belongs to the following groups of compounds:

isoparaffins with a dynamic viscosity of less than 0.5 Pa·s, corresponding to the formula:

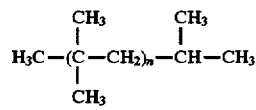

in which n is between 2 and 16, and their mixtures with oils of identical structure, in which n is greater than 18 and preferably between 18 and 40; such oils are sold by the Company Presperse Inc. under the names "Permethyl 99A, 101A, 102A, 104A and 106A", or by the Company ICI under the name "Arlamol HD"; mention may also be made of the "Isopars" sold by the Company Exxon Inc.;

the poly-α-olefins of polydecene type, which may or may not be hydrogenated; such products are sold by the Company Ethyl Corporation under the name "Ethylflo"; mention is also made of polyisobutylenes, which may or may not be hydrogenated.

When the emulsion contains silicones, the latter are organopolysiloxanes, such as organopolysiloxane oils or organic solutions containing organosiloxane gums and/or resins.

Mention may be made, among these silicones, of volatile silicones having a boiling point between 60° C. and 260° C., such as cyclic silicones containing from 3 to 7 silicon atoms or linear volatile silicones having from 2 to 9 silicon atoms and having a kinematic viscosity of less than or equal to $5 \times 10^{-6}$ m²/s at 25° C.

The nonvolatile silicones are composed mainly of polyalkylsiloxanes, polyarylsiloxanes, polyalkylarylsiloxanes, copolymers of polyethersiloxanes, which may or may not be modified, silicone gums and resins and organo-modified polysiloxanes, as well as their mixtures.

Mention may be made, among polyalkylsiloxanes, of:

linear polydimethylsiloxanes with a kinematic viscosity greater than $10^{-1}$ m²/s which may contain trimethylsilyl, trihydroxysilyl or hydroxydimethylsilyl end groups;

polyalkylarylsiloxanes, such as linear and/or branched polydimethylphenylsiloxanes or polymethyldiphenylsiloxanes with a kinematic viscosity of $10^{-5}$ to $5.10^{-2}$ m²/s at 25° C.;

poly($C_{10}$–$C_{30}$)alkylsiloxanes containing trimethylsilyl end groups;

copolymers of polyethersiloxanes, which may or may not be modified, are [sic] chosen in particular from copolymers of ethylene oxide and/or of propylene oxide with a diorganosiloxane, such as dimethicone copolyols;

silicone gums are [sic], inter alia, polydiorganosiloxanes with a molecular mass of between 200,000 and 1,000,000, used alone or as a mixture, in a solvent chosen from volatile silicones, polydimethylsiloxane oils, polyphenylmethylsiloxane oils, isoparaffins, dodecane, tridecane, tetradecane or their mixtures;

organopolysiloxane resins which can be used in accordance with the invention are [sic] crosslinked siloxane systems containing $R_2SiO_{2/2}$, $RSiO_{3/2}$ and $SiO_{4/2}$ units in which R represents a hydrocarbon group having from 1 to 6 carbon atoms or a phenyl group; the hydrocarbon group preferably denotes a $C_1$–$C_4$ alkyl radical;

organomodified silicones are [sic] chosen in particular from the abovementioned silicones containing in their general structure one or a number of organo-functional groups attached directly to the siloxane chain or attached via a hydrocarbon radical. Mention may be made, for this purpose, of silicones containing perfluorinated groups, such as trifluoroalkyl groups, hydroxylated groups, such as polyorganosiloxanes containing hydroxyalkyl functional groups, alkoxylated groups or acyloxyalkyl groups.

Particularly preferred polyorganosiloxanes are chosen from:

nonvolatile silicones of the linear polyalkylsiloxane type containing trimethylsilyl end groups, like the "Silbione" oils of the 70 047 and 47 series, such as 47V 500.000 oil, marketed by the Company Rhône-Poulenc, or the "DC 200 Fluid" oil from the Company Dow Corning;

mixtures of organopolysiloxanes and of volatile cyclic silicones such as the products Q2 1 401 or Q2 3225C from the Company Dow Corning or SF 1214 Silicone Fluid from the Company General Electric;

dimethicone copolyols such as the product Q2 5220 from the Company Dow Corning;

fluorosilicones of polyalkylsiloxane type containing trimethylsilyl end groups and substituted on the chain by trifluoropropyl groups, such as the fluorosilicone sold by the Company Shin Etsu under the name "X 22-821";

linear or cyclic volatile silicones and more particularly decamethylcyclopentasiloxane and its mixtures, for example the products "DC 245 Fluid" and "DC 345 Fluid" from the Company Dow Corning.

According to a preferred embodiment, the cosmetic emulsion according to the invention contains fat-soluble or water-soluble UV-B and/or UV-A sunscreens. It may also contain polymer screening agents and/or silicone screening agents, such as those described in French Patent Application No. 2,680,683.

The sunscreens are chosen in particular from cinnamic derivatives, such as, for example, 2-ethylhexyl p-methoxycinnamate; salicylic derivatives, such as, for example, 2-ethylhexyl salicylate; camphor derivatives, such as, for example, (4-methylbenzylidene)camphor or benzene-1,4-[di(3-methylidene-10-camphorsulfonic)] [sic] acid; benzimidazole derivatives, such as 2-phenylbenzimidazole-5-sulfonic acid; triazine derivatives, such as 2,4,6-tris[p-(2'-ethylhexyl-1'-oxycarbonyl)anilino)-1,3,5-triazine [sic]; benzophenone derivatives, such as 2-hydroxy-4-methoxybenzophenone; dibenzoylmethane derivatives, such as 4-tert-butyl-4'-methoxydibenzoylmethane, or β,β-diphenylacrylate derivatives, such as 2-ethylhexyl α-cyano-β,β-diphenylacrylate.

These sunscreens are used in proportions of between 0.01 and 15% by weight with respect to the total weight of the emulsion.

In addition to water, the cosmetic emulsion according to the invention may contain, as solvents, up to 5% by weight, on the basis of the total weight of the emulsion, of one or a number of alkylene glycols, for example ethylene glycol, propylene glycol and diethylene glycol.

The emulsion in accordance with the invention may also contain any other adjuvant commonly used in cosmetic compositions for the skin and more particularly humectants, such as polyols, for example glycerin or sorbitol, metal oxide pigments and nanopigments, emollients, vitamins, antioxidants, agents for stabilizing the primary emulsion, for example sodium chloride, magnesium chloride, magnesium sulfate or the product named "Elfacos C 26", sold by the Company Akzo Chemie, which is an ester of hydroxyoctacosanyl alcohol and of hydroxystearic acid, and fragrances and preservatives.

The solvents, fatty substances or adjuvants used in the emulsions in accordance with the invention must not contain either a primary or secondary amine group or an oxidizing group capable of interfering with DHA.

The emulsion according to the invention may also contain, or be used jointly with, substances which can have a tinting or additional coloring effect on the skin in combination with the DHA. To this end, it is possible in particular to use hydroxyindoles or melanin pigments of natural or synthetic origin.

The process for coloring the skin which is another subject of the invention is essentially characterized in that an emulsion as defined above is applied to the skin in amounts which are sufficient to confer on the skin a coloring which is similar to natural tanning.

The examples which follow are intended to illustrate the invention without having any limiting nature.

EXAMPLE 1—W/O EMULSION

| Emulsifier: | |
|---|---|
| Polyoxyethylenated (2.5 mol of ethylene oxide) and polyoxypropylenated (1.5 mol of propylene oxide) derivative of a mixture of the glycerol and of the sorbitol esters of hydroxystearic and isostearic acids, sold under the name "Arlacel 780" by the Company ICI | 3.0 g |
| DHA | 4.0 g |
| Stabilizers: | |
| Magnesium sulfate 7H$_2$O | 0.7 g |
| "Elfacos C$_{26}$" from Akzo Chemie | 3.0 g |
| Poly-α-olefin: | |
| Hydrogenated polydecene sold under the name "Ethylflo 362 NF" by the Company Ethyl Corporation | 7.0 g |
| Dimethicone copolyol sold under the name "Q$_2$ 5220 [sic]" by the Company Dow Corning | 5.0 g |
| Preservatives, fragrances | q.s. |
| Water | q.s. for 100 g |

The aqueous phase is heated to 70° C. The fatty phase is also heated to 70° C.

The emulsion is produced by adding the aqueous phase to the fatty phase with vigorous stirring using a Moritz. When the temperature of the emulsion falls to approximately 40° C., the DHA, dissolved beforehand in approximately 10 g of water, is added. Stirring is continued. Finally, the silicone and then the preservative and fragrances are added. Stirring is continued until the emulsion has completely cooled.

EXAMPLE 2—W/O EMULSION

| Emulsifier: | |
|---|---|
| "Arlacel 780" | 3.0 g |
| DHA | 4.0 g |
| Stabilizers: | |
| Magnesium sulfate 7H$_2$O | 0.7 g |
| "Elfacos C$_{26}$" from Akzo Chemie | 3.0 g |
| Poly-α-olefin: | |
| Hydrogenated polydecene sold under the name "Ethylflo 362 NF" by the Company Ethyl Corporation | 7.0 g |
| Preservatives, fragrances | q.s. |
| Water | q.s. for 100 g |

EXAMPLE 3—W/O EMULSION

| Emulsifier: | |
|---|---|
| "Arlacel 780" | 4.0 g |
| DHA | 6.0 g |
| Stabilizers: | |
| Magnesium sulfate 7H$_2$O | 0.7 g |
| "Elfacos C$_{26}$" from Akzo Chemie | 3.0 g |
| Isoparaffin: | |
| Isododecane sold under the name "Permethyl 99A" by the Company Presperse Inc. | 9.0 g |
| Decamethylcyclopentasiloxane sold under the name "DC 245 Fluid" by the Company Dow Corning | 7.0 g |
| Preservatives, fragrances | q.s. |
| Water | q.s. for 100 g |

EXAMPLE 4—W/O EMULSION

| Emulsifier: | |
|---|---|
| "Arlacel 780" | 6.0 g |
| DHA | 2.5 g |
| Stabilizers: | |
| Magnesium sulfate 7H$_2$O | 0.7 g |
| "Elfacos C$_{26}$" from Akzo Chemie | 3.0 g |
| 2-Decanoxyundecanol [sic] sold under the name "Exxal 21" by the Company Exxon | 6.0 g |
| Mixture of dimethiconol (13%), of octamethylcyclotetrasiloxane and of decamethylcyclopentasiloxane (87%) sold under the name "Q$_2$-1401 [sic]" by the Company Dow Corning | 4.0 g |
| Poly-α-olefin: | |
| Hydrogenated polydecene sold under the name "Ethylflo 168" by the Company Ethyl Corporation | 6.0 g |
| Preservatives, fragrances | q.s. |
| Water | q.s. for 100 g |

EXAMPLE 5—TRIPLE W/O/W EMULSION

| A-Primary W/O emulsion | |
|---|---|
| Emulsifier: | |
| "Arlacel 780" | 3.0 g |
| DHA | 5.0 g |
| Isoparaffin: | |
| Heptamethylnonane sold under the name "Arlamol HD" by the Company ICI | 5.0 g |
| Polydimethylsiloxane with a viscosity of $10^{-2}$ m$^2$/s sold under the name "DC 200 Fluid" by the Company Dow Corning | 5.0 g |
| Glycerin | 3.0 g |
| Preservatives, fragrances | q.s. |
| Water | q.s. for 60 g |
| B-Triple W/O/W emulsion | |
| EO/PO Block copolymer (Poloxamer 407) sold by the Company ICI under the name "Symperonic PE/F 127" | 1.0 g |
| Glycerin | 2.0 g |
| Hydroxyethylcellulose sold under the name "Natrosol 250 HHR" by the Company Aqualon | 0.3 g |
| Preservatives, fragrances | q.s. |
| Water | q.s. for 100 g |

The primary W/O emulsion is prepared. The secondary emulsifier, consisting of the "Symperonic PE/F127", is brought to 80° C. in 18 g of water. A gel is prepared with the "Natrosol 250 HHR" in the remaining water. The "Natrosol" gel is added to the "Symperonic PE/F127" solution and then glycerin, preservative and fragrances are added, at 20° C. The primary emulsion is then added to the gelled aqueous phase. Stirring is applied until the W/O/W emulsion is obtained.

EXAMPLE 6—W/O EMULSION

| Emulsifier: | |
|---|---|
| "Arlacel 780" | 5.0 g |
| Isoparaffin: | |
| Heptamethylnonane sold under the name "Arlamol HD" by the Company ICI | 10.0 g |
| Stabilizers: | |
| Magnesium sulfate 7H$_2$O | 0.7 g |
| "Elfacos C$_{26}$" from Akzo Chemie | 3.0 g |
| Mixture of cyclic silicones: | |
| decamethyl-cyclopentasiloxane/octamethylcyclotetrasiloxane/dodecamethylcyclohexasiloxane sold under the name "DC 200 Fluid" by the Company Dow Corning (62 to 72/4/24) | 5.0 g |
| Mixture of polydimethylsiloxane containing polyoxyethylenated or polyoxypropylenated side chains (dimethicone copolyol) and of a cyclic polydimethylsiloxane, sold under the name "Q$_2$-3225 [sic]" by the Company Dow Corning | 5.0 g |
| Glycerin | 3.0 g |
| DHA | 5.0 g |
| Preservatives, fragrances | q.s. |
| Water | q.s. for 100 g |

EXAMPLE 7—W/O EMULSION

| Emulsifier: | |
|---|---|
| "Arlacel 780" | 5.0 g |
| Isoparaffin: | |
| "Arlamol HD" | 15.0 g |
| Mixture of cyclic silicones "DC 345 Fluid" from Dow Corning | 10.0 g |
| Stabilizers: | |
| Magnesium sulfate 7H$_2$O | 0.7 g |
| "Elfacos C$_{26}$" from Akzo Chemie | 3.0 g |
| DHA | 5.0 g |
| Preservatives, fragrances | q.s. |
| Water | q.s. for 100 g |

I claim:

1. Stable water-in-oil cosmetic emulsion for coloring the skin, characterized in that it comprises:
   A) 50 to 92% by weight, on the basis of the total weight of emulsion, of an aqueous phase comprising 0.5 to 10% by weight of dihydroxyacetone, on the basis of the total weight of the emulsion, and
   B) 8 to 50% by weight, on the basis of the total weight of the emulsion, of a fatty phase comprising 5 to 15% by weight of isoparaffin or of poly-α-olefin and 3 to 7% by weight of an emulsifier consisting of a mixture of sorbitol and of glycerol esters of saturated or unsaturated, straight- or branched-chain C$_{18}$ fatty acids, optionally containing a hydroxyl, these esters being oxyethylenated and oxypropylenated, the total number of ethylene oxide and of propylene oxide units being less than or equal to 5, all the percentages being given on the basis of the total weight of the emulsion.

2. Cosmetic emulsion according to claim 1, characterized in that dihydroxyacetone is used in proportions of between 1 and 7% by weight with respect to the total weight of the emulsion.

3. Cosmetic emulsion according to claim 1, characterized in that it additionally contains up to 10% by weight of silicone.

4. Cosmetic emulsion according to claim 1, characterized in that it additionally contains up to 15% by weight of fatty substances chosen from C$_8$–C$_{22}$ fatty acids, fatty alcohols, fatty acid esters and triglycerides of C$_6$–C$_{18}$ fatty acids.

5. Cosmetic emulsion according to claim 1, characterized in that the isoparaffin is chosen from isoparaffins with a dynamic viscosity of less than 0.5 Pa·s corresponding to the formula:

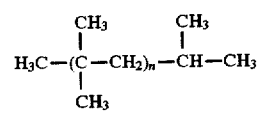

in which n is between 2 and 16, and their mixtures with oils of identical structure in which n is greater than 18 and preferably between 18 and 40.

6. Cosmetic emulsion according to any one of claims 1 to 4, characterized in that the poly-α-olefin is chosen from poly-α-olefins of polydecene type, which are hydrogenated or are not hydrogenated, and polyisobutylene, which are hydrogenated or are not hydrogenated.

7. Cosmetic emulsion according to claim 3, characterized in that the silicone is chosen from cyclic or linear volatile silicones having a boiling point of between 60° and 260° C. and nonvolatile silicones composed of polyalkylsiloxanes, polyarylsiloxanes, polyalkylarylsiloxanes, copolymers of polyethersiloxanes which may or may not be modified, silicone gums and resins and organomodified siloxanes, and their mixtures.

8. Cosmetic emulsion according to claim 1, characterized in that the emulsifier is a polyoxyethylenated, containing 2.5 mol of ethylene oxide, and polyoxypropylenated, containing 1.5 mol of propylene oxide, derivative of a mixture of the glycerol and of the sorbitol esters of hydroxy [sic] stearic and isostearic acids.

9. Cosmetic emulsion according to claim 1, characterized in that it also contains fat-soluble or water-soluble UV-B or UV-A sunscreens.

10. Cosmetic emulsion according to claim 9, characterized in that the sunscreens are chosen from cinnamates, salicylates, benzylidene camphor derivatives, benzimidazole derivates, triazine derivatives, benzophenone derivatives, dibenzoylmethane derivatives, β,β-diphenylacrylate derivatives, polymer screening agents and silicone screening agents.

11. Cosmetic emulsion according to claim 1, characterized in that it contains cosmetically acceptable adjuvants chosen from solvents of the alkylene glycol type, humectants of the polyol type, emollients, vitamins, antioxidants, agents for stabilizing the primary emulsion, fragrances and preservatives, and metal oxide pigments and nanopigments.

12. Triple water-in-oil-in-water cosmetic emulsion, characterized in that it comprises 55 to 80% by weight, on the basis of the total weight of the triple emulsion, of primary W/O emulsion according to claim 1 in 45 to 20% by weight, on the basis of the total weight of the triple emulsion, of a continuous external aqueous phase containing 0.75 to 2% by weight, on the basis of the total weight of the triple emulsion, of an emulsifier of the poly(ethylene oxide)/poly(propylene oxide) block copolymer type and optionally a thickener.

13. Process for coloring the skin in order to confer on it a tanning similar to natural tanning, characterized in that a water-in-oil or water-in-oil-in-water emulsion as defined in claim 1 is applied to the skin.

* * * * *